(12) United States Patent
Barry

(10) Patent No.: US 9,339,301 B2
(45) Date of Patent: *May 17, 2016

(54) SYSTEM AND METHOD FOR ALIGNING VERTEBRAE IN THE AMELIORATION OF ABERRANT SPINAL COLUMN DEVIATION CONDITIONS

(71) Applicant: Mark A. Barry, Haiku, HI (US)

(72) Inventor: Mark A. Barry, Haiku, HI (US)

(73) Assignee: Mark A. Barry, Las Vegas, NV (US)

( * ) Notice: Subject to any disclaimer, the term of this patent is extended or adjusted under 35 U.S.C. 154(b) by 552 days.

This patent is subject to a terminal disclaimer.

(21) Appl. No.: 13/645,589

(22) Filed: Oct. 5, 2012

(65) Prior Publication Data

US 2014/0100611 A1 Apr. 10, 2014
US 2016/0081720 A9 Mar. 24, 2016

Related U.S. Application Data

(63) Continuation of application No. 12/857,320, filed on Aug. 16, 2010, now Pat. No. 8,361,121, which is a continuation of application No. 11/202,409, filed on Aug. 10, 2005, now Pat. No. 7,776,072, which is a continuation-in-part of application No. 11/027,026, filed on Dec. 30, 2004, now Pat. No. 7,670,358.

(51) Int. Cl.
*A61B 17/70* (2006.01)
(52) U.S. Cl.
CPC ......... *A61B 17/7032* (2013.01); *A61B 17/7077* (2013.01)
(58) Field of Classification Search
CPC .................. A61B 17/7032; A61B 17/7077

USPC ................................................ 606/279, 265
See application file for complete search history.

(56) References Cited

U.S. PATENT DOCUMENTS

| 5,102,412 A | 4/1992 | Rogozinski |
| 5,112,332 A | 5/1992 | Cozad et al. |
| 5,116,334 A | 5/1992 | Cozad et al. |
| 5,181,917 A | 1/1993 | Rogozinski |

(Continued)

FOREIGN PATENT DOCUMENTS

| DE | 10125717 | 12/2002 |
| EP | 0553782 | 4/1993 |

(Continued)

OTHER PUBLICATIONS

Richard P. Schlenk, M.D., et al.; "Biomechanics of spinal deformity"; Department of Neurosurgery; Neurosurg. Focus 14(1); Article 2, pp. 1-15, Jan. 2003.

(Continued)

*Primary Examiner* — Ellen C Hammond
(74) *Attorney, Agent, or Firm* — Shay Glenn LLP

(57) ABSTRACT

A system and method for ameliorating spinal column anomalies, such as scoliosis, includes bone screws which are to be implanted in the pedicle region(s) of individual to-be-derotated vertebrae and in vertebrae to which balancing forces must be applied as the spinal column is derotated en mass to achieve an over-all correction of the condition. A pedicle screw cluster derotation tool simultaneously engages multiple pedicle screws and transmits rotative forces to multiple vertebrae to effect a whole-spine correction. Precontoured spinal rods are engaged post-derotation to secure the correction.

10 Claims, 5 Drawing Sheets

(56) References Cited

U.S. PATENT DOCUMENTS

| | | | |
|---|---|---|---|
| 5,306,275 | A | 4/1994 | Bryan |
| 5,466,238 | A | 11/1995 | Lin |
| 5,498,262 | A | 3/1996 | Bryan |
| 5,545,166 | A | 8/1996 | Howland |
| 5,630,816 | A | 5/1997 | Kambin |
| 5,676,665 | A | 10/1997 | Bryan |
| 5,704,937 | A | 1/1998 | Martin |
| 5,772,661 | A | 6/1998 | Michelson |
| 5,797,910 | A | 8/1998 | Martin |
| 5,810,817 | A | 9/1998 | Roussouly et al. |
| 5,928,232 | A | 7/1999 | Howland et al. |
| 5,947,965 | A | 9/1999 | Bryan |
| 6,015,409 | A | 1/2000 | Jackson |
| 6,090,113 | A | 7/2000 | Le Couedic et al. |
| 6,235,028 | B1 | 5/2001 | Brumfield et al. |
| 6,267,765 | B1 | 7/2001 | Taylor et al. |
| 6,375,657 | B1 | 4/2002 | Doubler et al. |
| 6,440,132 | B1 | 8/2002 | Jackson |
| 6,458,131 | B1 | 10/2002 | Ray |
| 6,558,390 | B2 | 5/2003 | Cragg |
| 6,652,526 | B1 | 11/2003 | Arafiles |
| 6,743,231 | B1 | 6/2004 | Gray et al. |
| 6,749,614 | B2 | 6/2004 | Teitelbaum et al. |
| 6,755,828 | B2 | 6/2004 | Shevtsov et al. |
| 6,802,844 | B2 | 10/2004 | Ferree |
| 6,821,277 | B2 | 11/2004 | Teitelbaum |
| 6,827,719 | B2 | 12/2004 | Ralph et al. |
| 7,188,626 | B2 | 3/2007 | Foley et al. |
| 7,670,358 | B2 * | 3/2010 | Barry .......................... 606/279 |
| 7,776,072 | B2 * | 8/2010 | Barry .......................... 606/265 |
| 7,794,464 | B2 | 9/2010 | Bridwell et al. |
| 7,951,175 | B2 | 5/2011 | Chao et al. |
| 8,147,524 | B2 | 4/2012 | Piza Vallespir |
| 2005/0033291 | A1 | 2/2005 | Ebara |
| 2005/0245928 | A1 * | 11/2005 | Colleran et al. ................ 606/61 |
| 2006/0149236 | A1 | 7/2006 | Barry |
| 2006/0195092 | A1 | 8/2006 | Barry |
| 2008/0294206 | A1 | 11/2008 | Choi et al. |
| 2009/0012565 | A1 | 1/2009 | Sachs et al. |
| 2010/0249844 | A1 | 9/2010 | Durrani |
| 2010/0312281 | A1 * | 12/2010 | Barry .......................... 606/264 |
| 2011/0172714 | A1 | 7/2011 | Boachie-Adjei et al. |
| 2011/0190820 | A1 | 8/2011 | Johansson et al. |
| 2012/0035668 | A1 | 2/2012 | Manninen et al. |
| 2012/0083853 | A1 | 4/2012 | Boachie-Adjei et al. |

FOREIGN PATENT DOCUMENTS

| | | |
|---|---|---|
| WO | WO 9410944 | 5/1994 |
| WO | WO 95/05786 | 3/1995 |
| WO | WO 9829046 | 7/1998 |
| WO | WO 2005089656 | 9/2005 |
| WO | WO 2005089657 | 9/2005 |
| WO | WO 2005092218 | 10/2005 |

OTHER PUBLICATIONS

U.S. Appl. No. 12/857,320; "System and Method for Aligning Vertebrae in the Amelioration of Aberrant Spinal Column Deviation Conditions", Aug. 16, 2010.

U.S. Appl. No. 12/980,737; "System and Method for Aligning Vertebrae in the Amelioration of Aberrant Spinal Column Deviation Conditions in Patents Requiring the Accommodation of Spinal Column Growth or Elongation", Dec. 29, 2010.

Medtronic's Motion to Disqualify, and associated Exhibits A-I, in *Mark A. Barry, MD v. Medtronic, Inc.*, Civil Action No. 1:14-cv-00104-RC, filed with the United States District Court for the Eastern District of Texas on Jun. 25, 2015 (703 pgs. total).

Order on Motion to Withdraw and Substitute Lead Counsel and Motion to Disqualify the Law firm, in *Mark Barry, M.D. v. Medtronic, Inc.*, Civil Action No. 1:14-cv-00104-RC, filed in the United States District Court for the Eastern District of Texas on Aug. 14, 2015.

Medtronic's Letter Brief requesting summary judgment of invalidity under 35 U.S.C. 102(b), and associated Exhibits, in *Mark A. Barry, MD v. Medtronic, Inc.*, Civil Action No. 1:14-cv-00104-RC, filed with the United States District Court for the Eastern District of Texas on Jun. 3, 2015.

Dr. Barry's Response to Medtronic's Letter Brief requesting summary judgment, and associated Exhibits, in *Mark A. Barry, MD v. Medtronic, Inc.*, Civil Action No. 1:14-cv-00104-RC, filed with the United States District Court for the Eastern District of Texas on Jun. 17, 2015.

Dr. Barry's Notice of Sur-Reply to Defendant's Reply, and associated Exhibits, in *Mark A. Barry, MD v. Medtronic, Inc.*, Civil Action No. 1:14-cv-00104-RC, filed with the United States District Court for the Eastern District of Texas on Jul. 10, 2015.

Dr. Barry's Response in Opposition to Motion to Disqualify, and associated Exhibits A-U, in *Mark A. Barry, MD v. Medtronic, Inc.*, Civil Action No. 1:14-cv-00104-RC, filed with the United States District Court for the Eastern District of Texas on Jul. 10, 2015.

Medtronic's First Amended Answer, Defenses, and Counterclaims, in *Mark A. Barry, MD v. Medtronic., Inc.*, Civil Action No. 1:14-cv-00104-RC, filed with the United States District Court for the Eastern District of Texas on Jul. 20, 2015.

Medtronic's Reply Memorandum of Law in Further Support of Its Motion to Disqualify, in *Mark A. Barry, MD v. Medtronic, Inc.*, Civil Action No. 1:14-cv-00104-RC, filed with the United States District Court for the Eastern District of Texas on Jul. 20, 2015.

\* cited by examiner

SYSTEM AND METHOD FOR ALIGNING VERTEBRAE IN THE AMELIORATION OF ABERRANT SPINAL COLUMN DEVIATION CONDITIONS

PRIORITY CITATION

This patent application is a Continuation of U.S. application Ser. No. 12/857,320, filed Aug. 16, 2010, which is a Continuation of U.S. application Ser. No. 11/202,409, filed Aug. 10, 2005 now U.S. Pat. No. 7,776,072 issued Aug. 17, 2010, which is a Continuation-in-Part application of U.S. patent application Ser. No. 11/027,026, filed Dec. 30, 2004 now U.S. Pat. No. 7,670,358, issued Mar. 2, 2010, the entire contents of which are incorporated by reference.

FIELD OF THE INVENTION

The present invention relates to methods and apparatus for management and correction of spinal deformities, such as scoliosis.

BACKGROUND OF THE TECHNOLOGY

A serious deficiency presently exists with respect to conventional treatment and instrumentation for treating spinal deviation anomalies, such as scoliosis.

This circumstance presents a serious medical challenge, because scoliosis, other than mild to moderate cases, is a well-recognized health risk.

If scoliosis curvature exceeds 70 degrees, severe twisting of the spine occurs. This can cause the ribs to press against the lungs, restrict breathing, and reduce oxygen levels. The distortions may also affect the heart and possibly cause dangerous changes.

Eventually, if the curve reaches more than 100 degrees, both the lungs and the heart can be injured. Patients with this degree of severity are susceptible to lung infections and pneumonia. Curves greater than 100 degrees are associated with elevated mortality rates. A number of factors associated with scoliosis increase the risk for bone loss, which is referred to as osteopenia. People with osteopenia are at greatly increased risk of osteoporosis, a common problem in older women that can cause broken bones and is particularly dangerous for women with a history of scoliosis. Experts recommend that children with scoliosis be screened for osteopenia so that measures can be taken to help prevent osteoporosis later.

Present treatment regimens for scoliosis carry their own risks and side effects, which include:

Spinal fusion disease. Patients who are surgically treated with fusion techniques lose flexibility and may experience weakness in back muscles due to injuries during surgery.

Disk degeneration and low back pain. With disk degeneration, the disks between the vertebrae may become weakened and may rupture.

Height loss.

Lumbar flatback. This condition is most often the result of a scoliosis surgical procedure called the Harrington technique, used to eliminate lordosis (exaggeration of the inward curve in the lower back). Adult patients with flatback syndrome tend to stoop forward. They may experience fatigue and back pain and even neck pain.

Rotational trunk shift (uneven shoulders and hips).

In some patients, years after the original surgery (particularly with the first generation of Harrington rods), the weight of the instrumentation can cause disk and joint degeneration severe enough to require surgery. Treatment may involve removal of the old instrumentation and extension of the fusion into the lower back.

Left untreated, or ineffectively treated, scoliosis carries long-term consequences.

Pain in adult-onset or untreated childhood scoliosis often develops because of posture problems that cause uneven stresses on the back, hips, shoulders, necks, and legs. Studies report, however, that patients with childhood scoliosis have the same incidence of back pain as the general population, which is very high (60% to 80%). In one study conducted 20 years after growth had stopped two-thirds of adults who had lived with curvatures of 20 to 55 degrees reported back pain. In this study, most cases were mild, although other studies have reported that adults with a history of scoliosis tend to have chronic and more back pain than the general population.

Nearly all individuals with untreated scoliosis at some point develop spondylosis, an arthritic condition in the spine. The joints become inflamed, the cartilage that cushions the disks may thin, and bone spurs may develop. If the disk degenerates or the curvature progresses to the point that the spinal vertebrae begin pressing on the nerves, pain can be very severe and may require surgery. Even surgically treated patients are at risk for spondylosis if inflammation occurs in vertebrae around the fusion site.

The consequences of scoliosis are limited to the physical realm. The emotional impact of scoliosis, particularly on young girls or boys during their most vulnerable years, should not be underestimated. Adults who have had scoliosis and its treatments often recall significant social isolation and physical pain. Follow-up studies of children with scoliosis who did not have strong family and professional support often report significant behavioral problems.

Older people with a history of scoliosis, even those whose conditions were corrected, should realize that some negative emotional events in adulthood may possibly have their roots in their early experiences with scoliosis. Many studies have reported that patients who were treated for scoliosis have limited social activities and a poorer body image in adulthood. Some patients with a history of scoliosis have reported a slight negative effect on their sexual life. Pain appears to be only a minor reason for such limitation. An early Scandinavian study reported that adults with scoliosis had fewer job opportunities and a lower marriage rate than the general population.

It is clear, then, that scoliosis treatment options are presently lacking, and untreated scoliosis (except for mild to lower-moderate cases) is not an acceptable alternative. There are many apparatus which are designed for attachment to, and positioning adjacent the spinal column, and in many instances, these apparatus are designed for use in treating spinal column anomalies, such as scoliosis. However, all known systems are limited by their design and known implementation modes on either arresting further deleterious rotation of the involved vertebrae, or fixing individual vertebrae once, by some means, they are brought to approximate a desired orientation and position.

Significant correction of severe scoliotic curvature to the point of approximating normal spinal configuration, particularly by a single process, is simply unknown in the art. This is, it is believed, the result of focus in the field on the positioning substantially seriatim of affected vertebrae. Applying derotational force to a vertebrae in this manner cannot effect en mass spinal reconfiguration without risking vertebral fracture at the point of spinal instrumentation fixation, particularly when using conventional instrumentation. Furthermore, significant, focused force applied to any individual vertebra risks spinal cord and related injury. Thus, only force which is inadequate to effect substantial correction to the entire spinal column is thus far ever applied, and correction of scoliotic curvatures are substantially limited.

It has become clear to the present inventor that desired levels of correction of spinal column anomalies, such as scoliosis, can only be achieved if the spinal column (or an affected segment thereof) is manipulated (or "derotated") substantially as a whole into a desired configuration. To achieve such an objective, force must be applied safely to all to-be-derotated vertebrae, and the forces necessary to reconfigure all, or at least a substantial portion of the spinal column must be dispersed throughout the affected spinal segments or regions. Nothing in the prior art satisfies these requirements, either individually or in combination.

SUMMARY OF THE INVENTION

In view of the foregoing, it is an object of the present invention to provide an improved system of spinal instrumentation for use in ameliorating aberrant spinal column deviation conditions, such as scoliosis.

It is another object of the present invention to provide an improved method for ameliorating aberrant spinal column deviation conditions, such as scoliosis. It is another object of the present invention to provide an improved system of spinal instrumentation, and a method for the use thereof, for ameliorating aberrant spinal column deviation conditions, such as scoliosis, which system and method facilitates the application of significant derotational forces to individual vertebra, with substantially reduced risk for fracture thereof upon application of such forces.

It is another object of the present invention to provide an improved system of spinal instrumentation, and associated method for use thereof, in ameliorating aberrant spinal column deviation conditions, such as scoliosis, which system and method facilitates the application of forces to vertebrae of affected spinal column segments en bloc, thereby distributing otherwise potentially injurious forces in a manner for safely achieving over-all spinal column correction or derotation.

Applicant's present invention provides a system and method for use of such system which satisfy each of these objectives. Applicant's system includes bone screws which are to be implanted in the pedicle region(s) of individual to-be-derotated vertebrae. In the preferred mode of the present invention, such bone screws are also to be implanted in vertebrae to which balancing forces must be applied as the spinal column is manipulated en mass to achieve an over-all correction of the condition. The pedicle implantation provides a stable foundation for the application of significant derotational forces, but without undue risk of vertebral fracture.

The system includes a pedicle screw cluster derotation tool. This tool, in the presently preferred embodiment includes shafts or similar pedicle screw engagement members, extending from a common handle or linked handle array, which are oriented and configured to extend to and engage the heads of a number of implanted pedicle screws which will have been implanted in adjacent vertebrae to which derotational or balancing forces are to be applied during a spinal column derotation and alignment. The engagement between the pedicle screw cluster derotation tool and the individual pedicle screws is such that, as manipulative forces are applied to the handle means of pedicle screw cluster derotation tool, forces are transferred and dispersed simultaneously among the engaged vertebrae. Therefore, a practitioner may, in a single motion, simultaneously and safely derotate multiple vertebrae of an affected spinal segment (as well as likewise apply balancing forces to other group(s) of vertebrae which are lateral to the effected segment(s).

The effect of practice of the present invention is three-dimensional correction which provides, not only spinal correction to near normal configuration, but corrects "rib humps."

The system of the present invention also includes, in its preferred embodiment, pedicle screws which allow for interfacing with, and fixation relative to pre-contoured spinal rods after a satisfactory derotation.

The present inventor's approach to the problems described above is certainly simple, when viewed in hindsight, but it is equally unobvious. In investigative procedures, the presently proposed system and method has achieved measure of correction of scoliotic curvature never before seen in orthopedic practice.

BRIEF DESCRIPTION OF THE DRAWINGS

The present invention may be more easily understood with reference to figures, which are as follow.

DETAILED DESCRIPTION OF THE PREFERRED EMBODIMENT

With reference to FIGS. 1-4 and 7, the spinal deviation correction system of the present invention includes a number of pedicle screws 10, each implanted in respective vertebrae to which rotative forces will be applied in a spinal anomaly correction.

Pedicle screws 10 may be of a variety of designs, such as, for example, are generally depicted in U.S. Pat. No. 6,743, 237 (Gray, et al), U.S. Pat. No. 6,827,719 (Ralph, et al), U.S.

Pat. No. 6,652,526 (Arafiles), U.S. Pat. No. 6,375,657 (Doubler, et al), the disclosures of which are incorporated herein by reference.

Figure 3:
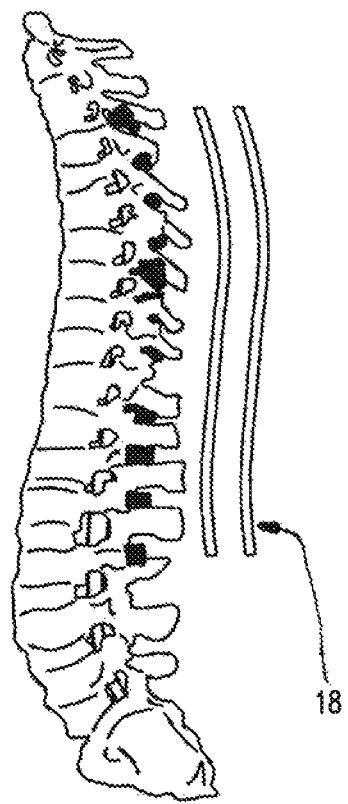
FIG. 3 is an elevational side view of the anatomical model of a human spinal column depicted in FIGS. 1 and 2, with an unobstructed view of already-implanted pedicle screws and adjacent, pre-contoured spinal rods which will be engaged with the pedicle screws through practice of the proposed method.
Figure 4:
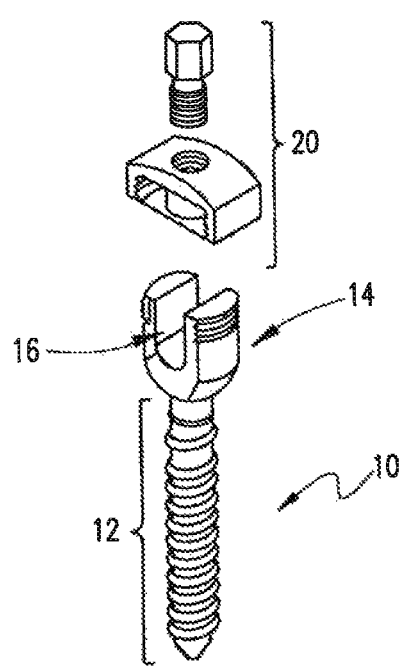
FIG. 4 is an example of a pedicle screw which may be used in the system of the present invention.

With particular reference to FIG. 4, pedicle screws 10 will include a threaded shank segment 12 and a head segment 14. Head segment will be configured with a spinal rod conduit (or channel) 16 or interfacing with a spinal rod 18 (shown in FIG. 3). Spinal rod engagement means 20 serve to fix pedicle screw 10 and spinal rod 18 in relative position and orientation, once a spinal column derotation is complete.

Figure 1:
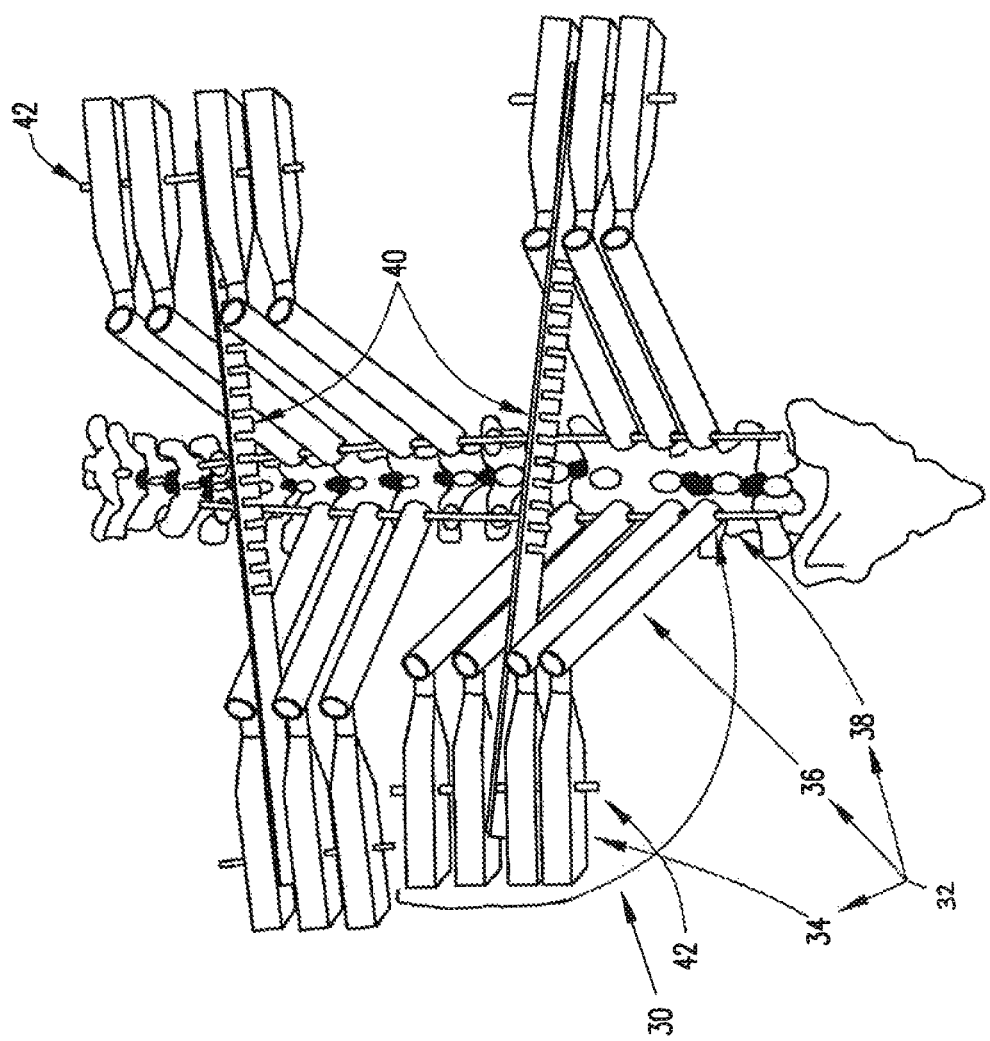
FIG. 1 is a top plan view of an anatomical model of a human spinal column, with components of the system of the present invention shown engaged therewith. The event depicted is that stage of the proposed method after which derotational and balancing forces have been applied to substantially correct a scoliotic curvature.
Figure 2:
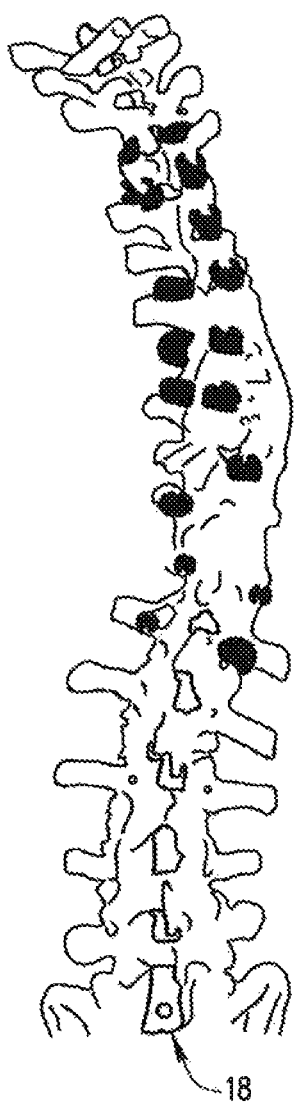
FIG. 2 is an elevational dorsal view of the anatomical model of a human spinal column depicted in FIG. 1, but with an unobstructed view of already-implanted pedicle screws, and configured as if preceding the derotation step of the proposed method.

Referring again, generally to FIGS. 1-4, and 7, the system of the present invention further includes a pedicle screw cluster derotation tool 30. As depicted in FIG. 1, each pedicle screw cluster derotation tool 30 is configured from a grouping of pedicle screw wrenches 32, by a pedicle screw wrench linking member 42 joined together to act in unison during use.

Each pedicle screw wrench 32 includes a handle 34, a shaft 36, and a distal end 38 which is configured to reversibly engage the head segment 14 of a pedicle screw 10 such that, as shaft 36 is moved while shaft distal end 38 is engaged with head segment 14, manipulative forces are transferred to the pedicle screw 10 and, in turn, to the vertebra in which such pedicle screw 10 is implanted.

Significant variations of pedicle screw cluster derotation tool 30 are contemplated by the present invention. For example, the multiple wrenches 32, linked by wrench cross linking members 40, depicted in FIG. 1 may be replaced by a single handle member from which extend the functional equivalent of the multiple shafts 36 and shaft distal ends 38 for simultaneously engaging multiple pedicle screws 10, as depicted. However configured, the object and design of pedicle screw cluster derotation tool 30 is to facilitate simultaneous application of manipulative forces to multiple pedicle screws 10 which are implanted in a like number of vertebra. This has the effect of permitting the gross, en bloc application of sufficient derotative forces to affected segments of the spinal column in a sufficiently dispersed manner as to avoid injury to any one vertebra or isolated spinal column segment. This, in turn, facilitates a successful entire-spine, 3D derotation of a scoliosis patient to near normal parameters.

Figure 5:
FIG. 5 is a depiction of the complimentary forces applied to multiple spinal column segments to achieve an over-all spinal column correction.
Figure 7:
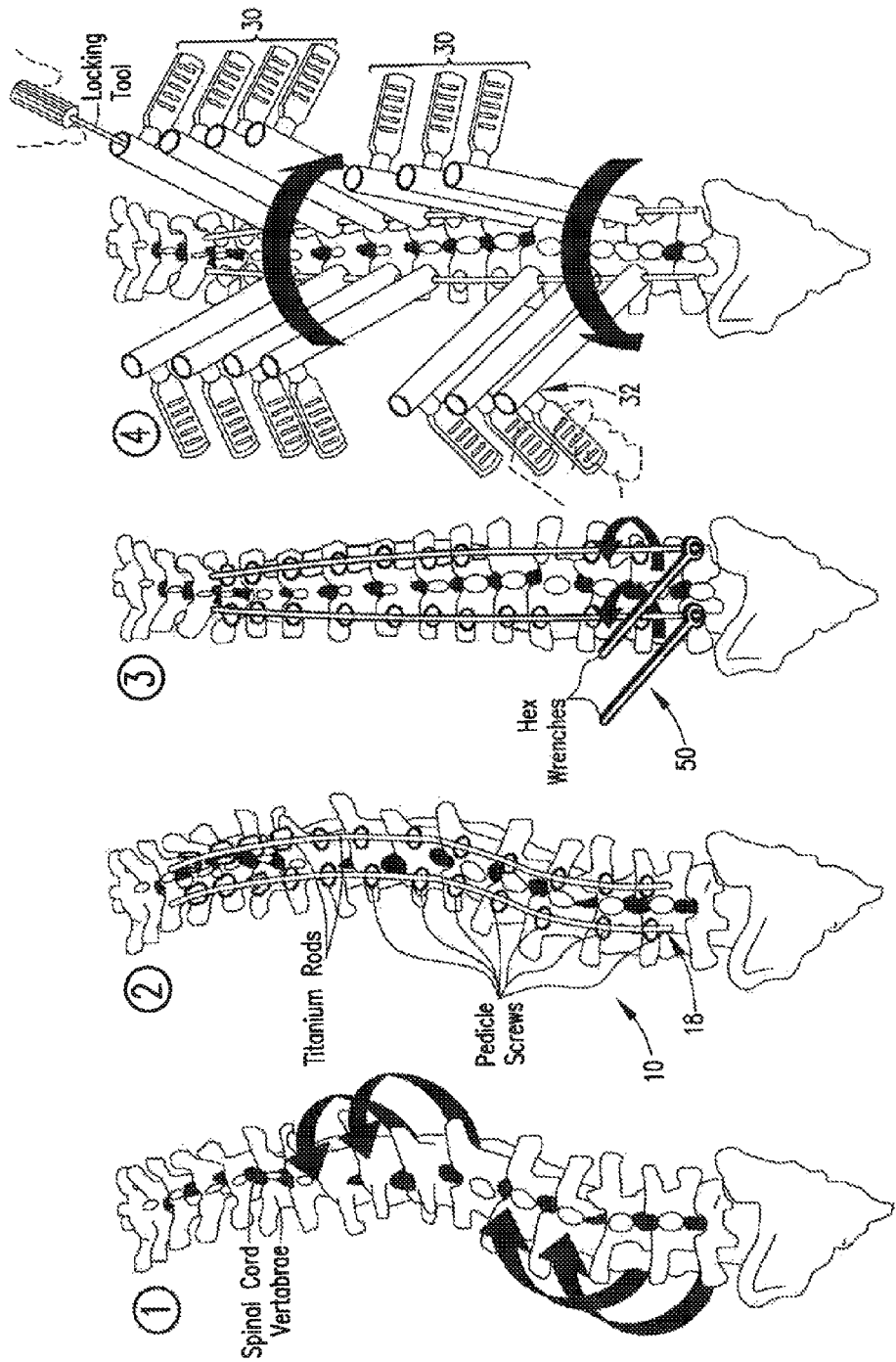
FIG. 7 is a 4-frame, progressive animation of the stages of correction of scoliosis according to the embodiments of the present invention.

With reference to FIGS. 1-3, 5 and 7 the preferred mode of the present method usually involves application of forces to multiple spinal column segments, to achieve an over-all spinal column correction. For example, as depicted in FIGS. 5 and 7 in the case of a single curvature case of scoliosis, both derotative forces (illustrated by the central force vector arrow of FIG. 5) to vertebrae involved in scoliotic curvatures, as well as of balancing, or offsetting forces to lateral spinal segments (illustrated by the lateral arrows of FIG. 5) are applied.

The preferred mode of the present method involves pre-contouring spinal rods member 18, as shown in FIG. 3 and frame 2 of FIG. 7. Such a contouring operation involves bending spinal rods member 18 such that, in along two axes (analogous to yaw and pitch in aviation terms), the spinal rods member 18 will substantially define, in one plane, a desired post-operative correction of the affected spinal column in reference to such two axes.

The spinal rod(s) member 18 are loosely engaged with pedicle screws 10, and in one of the embodiments of the present invention the pre-contoured spinal rod member 18 are rotated from a first orientation, through approximately 90° to a second orientation, using hex wrenches 50 (see frame 3 of FIG. 7), to achieve a substantial correction of the scoliosis in the first two of three axes which will be corrected according to one of the embodiments of the present methodology, through use of the present system.

The next phase, after 2-D correction as just described, involves applying manipulative forces to pedicle screw clusters in reference to a third axis (a "roll axis", again using aviation terms) using pedicle screw clusters derotation tool(s) 30 (see, inter alia, frame 4 of FIG. 7). After this final correction, spinal rod engagement member 20 is tightened to fix pedicle screw 10 and spinal rod 18 in relative position and orientation to secure the corrected spinal column configuration (now corrected with reference to all three relevant axes).

Spinal rod engagement member 20 of pedicle screws 10 are tightened, using an anti-torque feature of wrenches 32 (or of their equivalent in an alternative embodiment). This feature, as is well known in the art, allows tightening of nuts and the like, without imparting undue torque to the underlying apparatus or structure.

Figure 6:
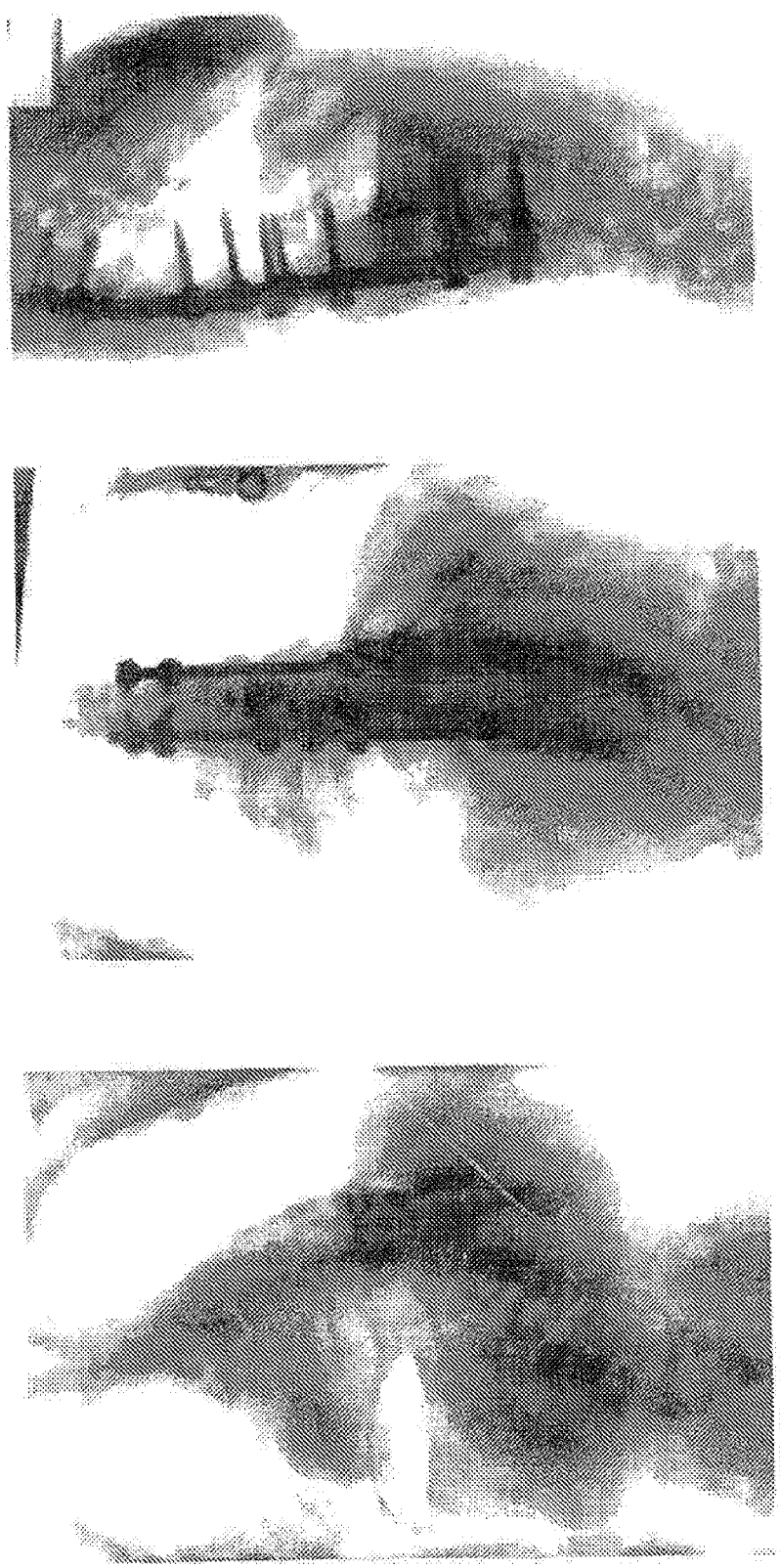
FIG. 6 is a three frame x-ray view showing "before and after" views of a scoliosis patient who was treated in an investigational procedure in the development of the systems and methods of the present disclosure. The curvature correction was substantially to normal, and lumbar motion was preserved notwithstanding.

As shown in FIG. 6, investigative practice of at least one of the present methods disclosed herein achieves efficacy never before seen in the orthopedic field. The "before picture" is the left hand image of FIG. 6, and the two remaining images are sagittal and dorsal views of the corrected spinal column.

Although the invention has been described with reference to specific embodiments, this description is not meant to be construed in a limited sense. Various modifications of the disclosed embodiments, as well as alternative embodiments of the inventions will become apparent to persons skilled in the art upon reference to the description of the invention. It is, therefore, contemplated that the appended claims will cover such modifications that fall within the scope of the invention.

What is claimed is:

1. A system for aligning human vertebrae comprising:
a first set of at least three pedicle screws, each pedicle screw having a threaded shank and a head, said first set of pedicle screws adapted to be implanted in a first group of at least three vertebrae;
a first pedicle screw cluster derotation tool adapted to facilitate simultaneous application of rotative force in a single motion to said first group of at least three vertebrae, said first pedicle screw cluster derotation tool having a first set of at least three pedicle screw engagement members configured to engage the heads of the corresponding first set of at least three pedicle screws, said first set of pedicle screw engagement members being interconnected by a first linking member such that application of rotative force in the single motion to said pedicle screw engagement members simultaneously moves all of the interconnected pedicle screw engagement members;
a second set of at least three pedicle screws, each pedicle screw of said second set of pedicle screws having a threaded shank and a head, said second set of pedicle screws adapted to be implanted in said first group of at least three vertebrae;
a second pedicle screw cluster derotation tool adapted to facilitate simultaneous application of rotative force in the single motion to said first group of at least three vertebrae, said second pedicle screw cluster derotation tool having a second set of at least three pedicle screw engagement members configured to engage the heads of the corresponding second set of at least three pedicle screws, said second set of pedicle screw engagement members being interconnected by a second linking member such that application of the rotative force in the single motion to one or more of the pedicle screw engagement members of said first or second set of pedicle screw engagement members simultaneously moves all of the respectively interconnected pedicle screw engagement members of said first and second set of pedicle screw engagement members; and
a cross-linking member interconnecting said first set of pedicle screw engagement members and said second set of pedicle screw engagement members;
wherein each pedicle screw engagement member of said first and second set of pedicle screw engagement members is configured to transmit the rotative force to said head of said pedicle screw to which said respective pedicle screw engagement member is engaged so as to be adapted to simultaneously rotate the vertebrae of the first group of at least three vertebrae.

2. The system of claim 1, further comprising a handle member configured to be coupled to one or more of said pedicle screw engagement members, said handle member in cooperation with said first linking member facilitating the simultaneous application of the rotative force to each pedicle screw of said first set of at least three pedicle screws.

3. The system of claim 1, wherein said simultaneous application of rotative force is adapted to be applied in a direction generally parallel to a transverse plane of an anatomy including said human vertebrae.

4. The system of claim 1, further comprising a spinal rod member, wherein one or more of said pedicle screws of said set of at least three pedicle screws each includes:
a spinal rod conduit formed substantially transverse of the length of each said pedicle screw and sized and shaped for receiving passage of said spinal rod member therethrough; and a spinal rod engagement member configured to threadably engage said head segment of each said pedicle screw and for securing each said pedicle and said spinal rod, when extending through said spinal rod conduit, in a substantially fixed relative position and orientation.

5. The system of claim 4 wherein the spinal rod is precontoured.

6. A method for aligning human vertebrae comprising:
selecting a first set of at least three pedicle screws, said pedicle screws each having a threaded shank and a head;
selecting a first pedicle screw cluster derotation tool, said first pedicle screw cluster derotation tool having a first set of at least three pedicle screw engagement members that are interconnected by a first linking member such that application of a rotative force to any one of said pedicle screw engagement members simultaneously moves each pedicle screw engagement member of said first set of pedicle screw engagement members, each pedicle screw engagement member being configured for engaging with, and transmitting rotative forces applied to said first pedicle screw cluster derotation tool to, said head of each pedicle screw of said first set of pedicle screws;
selecting a second set of at least three pedicle screws;
selecting a second pedicle screw cluster derotation tool, said second pedicle screw cluster derotation tool having a second set of at least three pedicle screw engagement members that are interconnected by a second linking member such that application of rotative force to any one of said pedicle screw engagement members of said second set of pedicle screw engagement members simultaneously moves each pedicle screw engagement member of said second set of pedicle screw engagement members, each pedicle screw engagement member of said second set of pedicle screw engagement members being configured for engaging with, and transmitting rotative forces applied to, said second pedicle screw duster cluster derotation tool to said head of each pedicle screw of said second set of pedicle screws;
implanting each pedicle screw of said first set of pedicle screws in a pedicle region of a first group of at least three vertebrae of a spinal column;
implanting each pedicle screw of said second set of pedicle screws in a pedicle region of each of a second group of three or more vertebrae of a spinal column;
engaging each said pedicle screw engagement members, respectively, with said head of each pedicle screw of said first set of pedicle screws;
engaging each said pedicle screw engagement members, respectively, with said head of each pedicle screw of said second set of pedicle screws;
applying rotative force to said first pedicle screw cluster derotation tool in a manner for simultaneously engaging each of said first set of pedicle screw engagement members and said first set of pedicle screws and thereby in a single motion simultaneously rotating said vertebrae of said first group of vertebrae in which said pedicle screws are implanted to achieve an amelioration of an aberrant spinal column deviation condition; and
applying rotative force to said second pedicle screw cluster derotation tool in a manner for simultaneously engaging said second set of pedicle screw engagement members and said second set of pedicle screws and thereby in a single motion simultaneously rotating said vertebrae of said second group of at least three vertebrae in which said second set of pedicle screws are implanted to achieve the amelioration of the aberrant spinal column deviation condition.

7. The method of claim 6, wherein selecting said first pedicle screw cluster derotation tool includes selecting said first pedicle screw cluster derotation tool having said first set of at least three pedicle screw engagement members and a handle member coupled to said first set of pedicle screw engagement members that are interconnected by the first linking member such that application of the rotative force to said handle member simultaneously moves each pedicle screw engagement member of said first set of pedicle screw engagement members.

8. The method of claim 6, further comprising:
selecting a first length of a spinal rod member, wherein one or more of said pedicle screws of said first set of pedicle screws each includes:
a spinal rod conduit formed substantially transverse of the length of said pedicle screw and sized and shaped for receiving passage of said spinal rod member therethrough; and
a spinal rod engagement member configured to threadably engage said head to secure said pedicle screw and said spinal rod member, when extending through said spinal rod conduit, in a substantially fixed relative position and orientation;
extending said first length of said spinal rod member through said spinal rod conduits of one or more of said pedicle screws of said first set of pedicle screws; and
after applying said rotative force to said first pedicle screw cluster derotation tool, actuating said spinal rod engagement member to secure said vertebrae in their respective and relative positions and orientations as achieved through application of said rotative force thereto.

9. The method of claim 6, wherein the steps of applying rotative force to the first pedicle screw cluster derotation tool and applying rotative force to the second pedicle screw cluster derotation tool are carried out substantially simultaneously to cooperatively achieve the amelioration of the aberrant spinal column deviation condition.

10. A system for aligning human vertebrae comprising:
a first set of at least three pedicle screws, each pedicle screw having a threaded shank and a head, said first set of pedicle screws adapted to be implanted in a first group of at least three vertebrae;
a second set of at least three pedicle screws, each pedicle screw of said second set of pedicle screws having a threaded shank and a head, said second set of pedicle screws adapted to be implanted in said first group of at least three vertebrae; and
a pedicle screw cluster derotation tool adapted to facilitate simultaneous application of rotative force in a single motion to said first group of at least three vertebrae, said pedicle screw cluster derotation tool including:
a first set of at least three pedicle screw engagement members configured to engage the heads of the corresponding first set of at least three pedicle screws, said first set of pedicle screw engagement members being interconnected by a first linking member such that application of the rotative force in the single motion to said first set of pedicle screw engagement members simultaneously moves all of the interconnected pedicle screw engagement members;
a second set of at least three pedicle screw engagement members configured to engage the heads of the corresponding second set of at least three pedicle screws, said second set of pedicle screw engagement members being interconnected by a second linking member such that application of the rotative force in the single motion to one or more of the pedicle screw engagement members of said first or second set of pedicle screw engagement members simultaneously moves all of the respectively interconnected pedicle screw engagement members of said first and second set of pedicle screw engagement members; and
a cross-linking member interconnecting said first set of pedicle screw engagement members and said second set of pedicle screw engagement members;
wherein each pedicle screw engagement member of said first and second set of pedicle screw engagement members is configured to transmit the rotative force to said head of said pedicle screw to which said respective pedicle screw engagement member is engaged so as to be adapted to simultaneously rotate the vertebrae of the first group of at least three vertebrae;
wherein said application of rotative force to one or more of said pedicle screw engagement members of said first or second set of pedicle screw engagement members is adapted to be applied in a direction generally parallel to a transverse plane of an anatomy including said human vertebrae.

* * * * *